US011612744B2

United States Patent
Chen et al.

(10) Patent No.: US 11,612,744 B2
(45) Date of Patent: Mar. 28, 2023

(54) HEAD CAP WITH CHANNEL IDENTIFICATION

(71) Applicants: Taipei Medical University, Taipei (TW); National Cheng Kung University, Tainan (TW)

(72) Inventors: Shih-Ching Chen, Taipei (TW); Chih-Wei Peng, Taipei (TW); Che-Wei Lin, Tainan (TW); Jia-Jin Chen, Tainan (TW); Chun-Wei Wu, Tainan (TW); Samuel Wang, Taipei (TW); Chun-Ie Wu, Tainan (TW); Nguyen Van Truong, Tainan (TW)

(73) Assignees: TAIPEI MEDICAL UNIVERSITY, Taipei (TW); NATIONAL CHENG KUNG UNIVERSITY, Tainan (TW)

( * ) Notice: Subject to any disclaimer, the term of this patent is extended or adjusted under 35 U.S.C. 154(b) by 41 days.

(21) Appl. No.: 17/127,433

(22) Filed: Dec. 18, 2020

(65) Prior Publication Data
US 2021/0213285 A1    Jul. 15, 2021

Related U.S. Application Data

(60) Provisional application No. 62/959,583, filed on Jan. 10, 2020.

(51) Int. Cl.
*A61N 1/04*     (2006.01)
*A61N 1/36*     (2006.01)
*A61N 1/05*     (2006.01)

(52) U.S. Cl.
CPC ....... *A61N 1/36025* (2013.01); *A61N 1/0456* (2013.01); *A61N 1/0484* (2013.01); *A61N 1/0526* (2013.01)

(58) Field of Classification Search
CPC .............. A61N 1/0456; A61N 1/36025; A61N 1/0526; A61N 1/0529; A61N 1/0484
See application file for complete search history.

(56) References Cited

U.S. PATENT DOCUMENTS

2013/0281759 A1*   10/2013  Hagedorn ..........  A61N 1/36025
                                                                  600/15

* cited by examiner

*Primary Examiner* — Alyssa M Alter
(74) *Attorney, Agent, or Firm* — Muncy, Geissler, Olds & Lowe, P.C.

(57) ABSTRACT

A head cap with channel identification includes a head cap, channel identification module, a controlling module, and electrical stimulation modules. The head cap includes the channels therein, and the head cap includes brain regions corresponding to the brain areas of the human being. The electrical stimulation modules disposed in the channels, and the channel identification modules disposed around the peripheral of the channels. The controlling module is electrically coupled to the channel identification modules. When the electrical stimulation modules disposed in some of the channels, the channel identification modules around the peripheral of the channels and the electrical stimulation module are constituted a circuit conduction status or a short circuit status, then the channel identification module transmits a signal to the controlling module to determine the desired sites of the electrical stimulation module where is corresponding to one of the brain areas of the human being according to the signal.

9 Claims, 8 Drawing Sheets

HEAD CAP WITH CHANNEL IDENTIFICATION

CROSS-REFERENCE TO RELATED APPLICATION

This application claims the benefit of U.S. provisional patent application No. 62/959,583, filed on Jan. 10, 2020, the content of which are hereby incorporated reference in their entirely.

FIELD OF THE INVENTION

The present invention relates to a transcranial electrical stimulation system, and particularly relates to a head cap with channel identification with the sensor is provided for identifying the human brain area, and according to the changes in cerebral cortical blood flow of the specific brain area of the human being to stimulate the human brain to active the brain area of the human being.

BACKGROUND OF THE INVENTION

A wider variety of mental and physical processes are controlled or influenced by neural activity in particular region of the brain. For example, the physical or cognitive functions are organized according to neural-functions in some areas of the brain (i.e., the sensory or motor cortices). Several areas of the brain appear to have distinct functions in most individuals. In the majority of people, for example, the area of the occipital lobes relates to vision, the regions of the left interior frontal lobes relate to language.

Many problems or abnormalities with body functions can be caused by damage, disease and/or disorders in the brain. Effectively treating such abnormalities may be very difficult. For example, a stroke is common condition that damages the brain. Strokes are generally caused by emboli (e.g., vessel obstructions), hemorrhages (e.g., vessel ruptures), or thrombi (e.g., vessel clotting) in the vascular system of a specific region of the brain, which in turn generally cause a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus drug treatment. For most patients, however, such treatments are not sufficient, and little can be done to improve the function of an affected body part beyond the limited recovery that generally occurs naturally without intervention.

Neural activity can be influenced by electrical energy that is supplied from a waveform generator or other type of device. Various patient perceptions and/or neural functions can thus be improved or inhibited by applying an electrical current to neural tissue. As a result, researchers have attempted to treat various neurological conditions using electrical stimulation signals to control or affect neural functions.

Some existing applications such as Transcranial Electrical Stimulation (TES), Deep Brain Stimulation (DBS), Vagal Nerve Stimulation (VNS), and Functional Electrical Stimulation (FES) attempt to treat particular neurological conditions using devices that provide electrical or magnetic energy to certain target locations. In such applications, electrodes are typically employed to deliver stimulation signals. The electrodes may be internal or external devices that are generally coupled to pulse generators by a set of wires.

For example, one existing technique involves implanting electrodes within a patient at a desired location for electrical stimulation and implanting an implantable pulse generator (IPG) at a remote location. The IPG provides the stimulation signals and electrical current flow through the electrodes. The IPG transfers signals to electrodes by way of a set of lead wires that are tunneled through bodily tissues. Unfortunately, tunneling through tissue may be surgically invasive and/or difficult. Moreover, after implantation, bodily motion may stress portions of tunneled lead wire, possibly adversely impacting system reliability.

In other forms of electrical stimulation, microstimulators may be employed to provide direct bipolar electrical stimulation to nerve or muscle tissue in an attempt to evoke a therapeutic response. The microstimulators are implanted at a target site y expulsion, such as through the lumen of a needle. In addition, the disadvantage for the direct bipolar electrical stimulation includes the risk of infection, and/or inconvenient recovery period.

SUMMARY OF THE INVENTION

It is an objective of the present invention is to provide a high-definition and high-density transcranial electronic stimulation system.

It is another objective of the present invention is to provide a transcranial electrical stimulation system using CES-NIRS (cranial electrical stimulation-near infrared spectroscopy) unit for detecting the change in cerebral cortical blood flow of the brain area of the human being.

It is another objective of the present invention is to provide a transcranial electrical stimulation system using a hybrid optrode for monitoring the desired position in situ, and the desired position of the measurement is the location for stimulating.

It is another objective of the present invention, the position of the brain area where is to be stimulated can be automatically determined through the channel identification mechanism.

It is another objective of the present invention is to provide a transcranial electrical stimulation system using a hybrid optrode, which are coaxially designed by optical probe and the electrode to perform electrical stimulation and detection the changes in cerebral cortical blood flow over the specific brain area.

According to above objectives, the present invention provides a transcranial electrical stimulation system which includes a plurality of electrical stimulation modules, a controlling module, a plurality of channel identification modules, and a power supply module. Each the plurality of electrical stimulation modules includes an electrode and an optical probe, in which one end of the electrode is used to contact the tissue such as brain area of the human being, and the current is passed through the electrode to stimulate the desired sites in the brain area. The controlling module is used to receive the signal of the changes in cerebral cortical blood flow from the optical probe, and the controlling module is used to adjust, control and provide the current intensity corresponding to the changes in cerebral cortical blood flow to the electrode, so that the electrode can perform the electrical stimulation procedure to stimulate the desired sites of the brain area with the current. Each the plurality of channel identification modules is used to identify the desired sites where each the plurality of electrical stimulation modules is located, in which each desired site is corresponding to the specific brain area of the human being. The power supply module is used to provide the energy for the operations of the transcranial electrical stimulation system.

The present invention also provides a head cap with channel identification, which includes a head cap, a plurality of channel identification modules, a controlling module, and a plurality of electrical stimulation modules. The head cap includes the plurality of channels therein, and the head cap also includes a plurality of brain regions corresponding to the brain of the human being. Each the plurality of electrical stimulation modules disposed in each the plurality of the channels, and the plurality of channel identification modules disposed around the peripheral of each the plurality of channels in the head cap. The controlling module is electrically coupled to each the plurality of channel identification modules. When each the plurality of electrical stimulation modules is disposed in some of the plurality of channels, the channel identification modules around the peripheral of each the plurality of channels and the electrical stimulation module are constituted a circuit conduction status or a short circuit status, then the channel identification module transmits a signal to the controlling modules, so that the controlling module determines that the desired sites of the electrical stimulation module where is corresponding to one of the plurality of brain areas of the human being according to the signal.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Some sample embodiments of the invention will now be described in greater detail. Nevertheless, it should be recognized that the present invention can be practiced in a wide range of other embodiments besides those explicitly described, and the scope of the present invention is expressly not limited except as specified in the accompanying claims.

Figure 1:
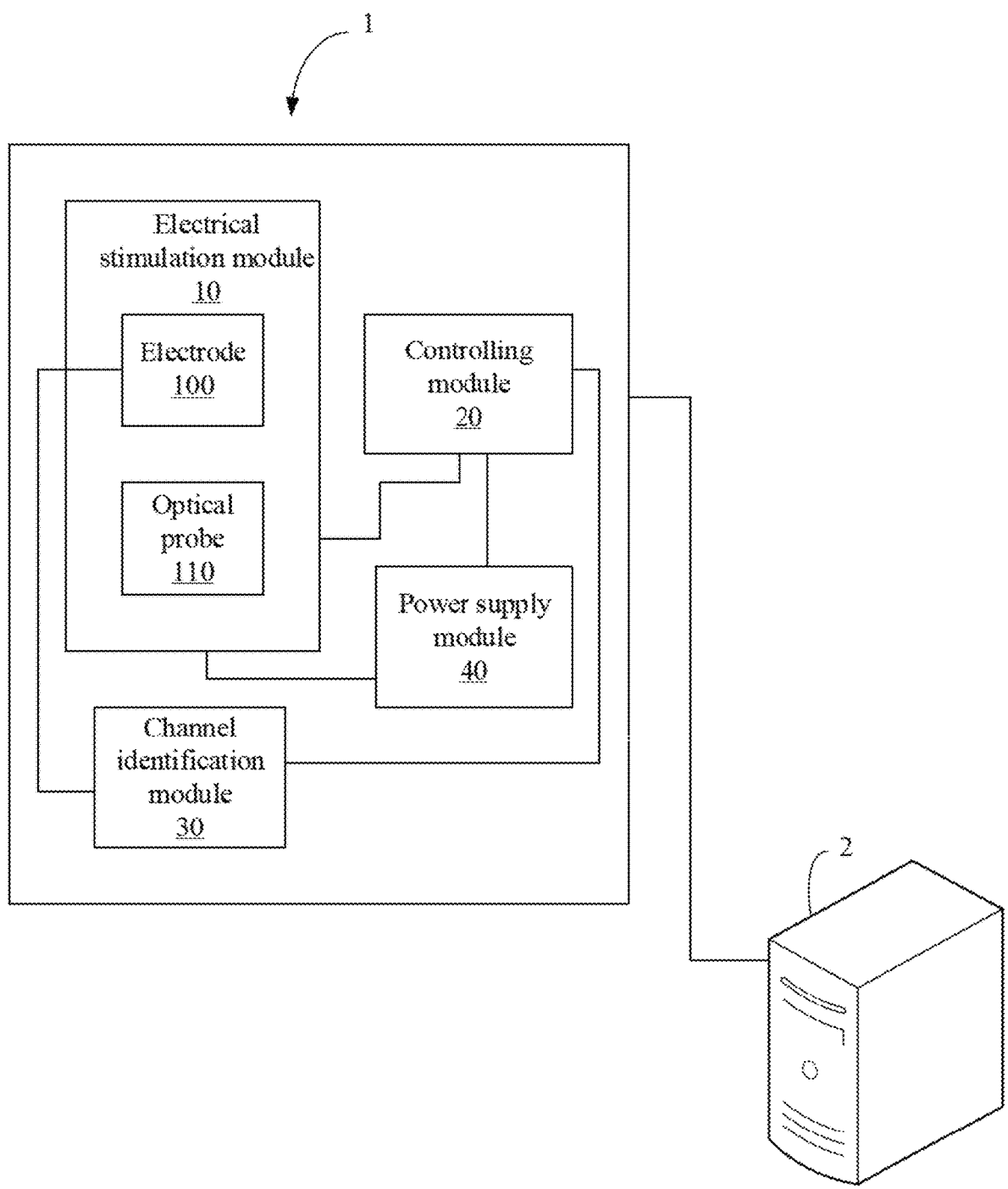
FIG. 1 is a schematic view of showing a block diagram of the transcranial electrical stimulation system in accordance with the present invention disclosed herein.

Please refer to FIG. 1. FIG. 1 shows a block diagram of the transcranial electrical stimulation system. In FIG. 1, the transcranial electrical stimulation system 1 includes a plurality of electrical stimulation modules 10, a controlling module 20, a plurality of channel identification modules 30, and a power supply module 40. Each the plurality of electrical stimulation modules 10 is composed of an electrode 100 and an optical probe 110. One end of the electrode 100 of each the plurality of electrical stimulation modules 10 is a contact end (not shown) which is used to contact the brain area (not shown) of the human being (not shown), and the current is passed through the contact end of the electrode 100 to stimulate the brain area of the human being where the desired sites is contacted by the contact end of the electrode 100. The optical probe 110 is used to detect the changes in cerebral cortical blood flow of the desired sites is contacted by the contact end of the electrode 100 in the brain area of the human being. In the preferred embodiment of the present invention, the optical probe 110 can be near infrared spectroscopy unit. When the optical probe 110 detects the changes in cerebral cortical blood flow over one of the brain areas of the human being, then the optical probe 110 transmits the signal of the changes in cerebral cortical blood flow to the controlling module 20. After the controlling module 20 received the signal of the changes in cerebral cortical blood flow detected by the optical probe 110, the controlling module 20 regulates the current intensity emitted by the electrical stimulation module 10 according to the amount of blood flow change measured by the optical probe 110, and transmits the current with this current intensity to the electrode 100, so that the electrode 100 can perform the electrical stimulation procedure to stimulate the desired sites of the brain area of the human being.

In one embodiment, when the optical probe 110 detects the changes in cerebral cortical blood flow of a specific brain area of the human being, the user can adjust or control the current intensity corresponding to the amount of the changes in cerebral cortical blood flow to stimulate the brain area of the human being by the external controlling device 2, such as computer or mobile device. In another preferred embodiment, user can makes the brain mapping table for the changes in cerebral cortical blood flow and the electrical field, so that when the optical probe 110 detects the amount of the changes in cerebral cortical blood flow, the controlling module 20 can adjust and control the current intensity based on the brain mapping table. In another preferred embodiment, the brain mapping table can be a software program previously written within the controlling module 20.

Figure 2:
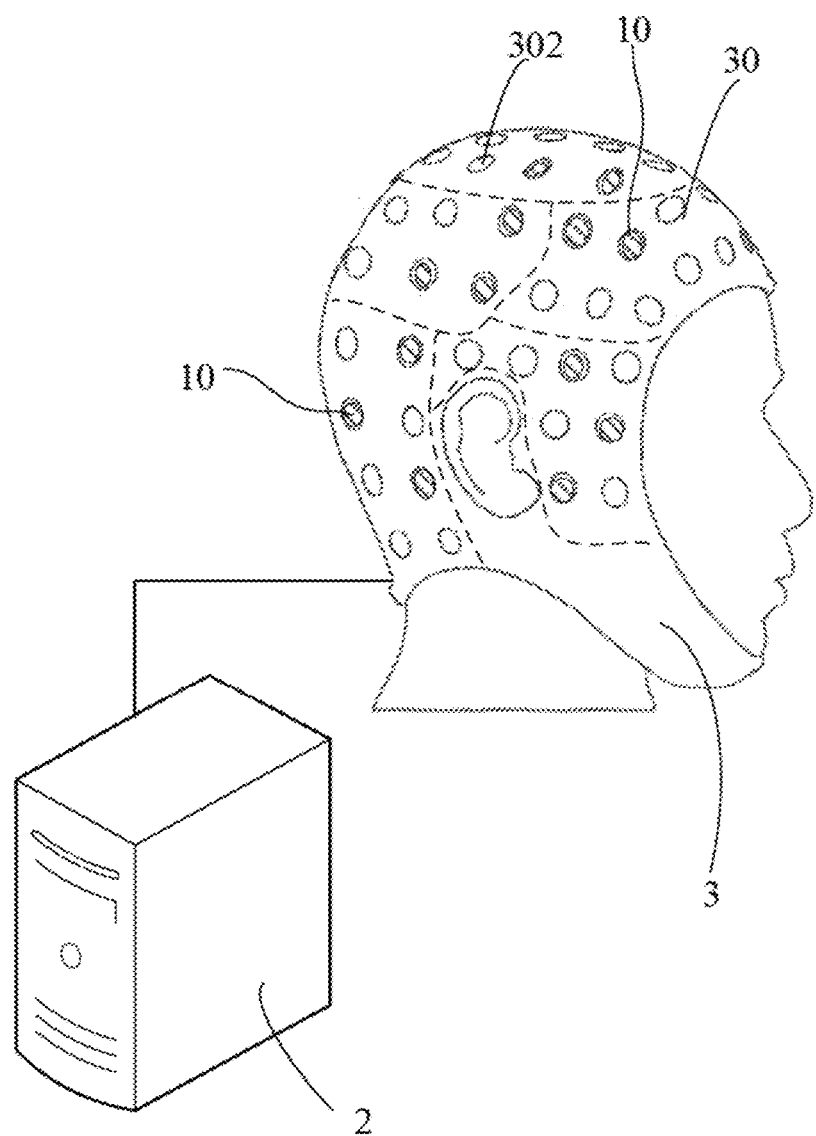
FIG. 2 is a schematic view of showing the head cap with the plurality of electrical stimulation modules electrically coupled to the external controlling device in accordance with the present invention disclosed herein.

Please continue to refer to FIG. 1 and FIG. 2. Each the plurality of channel identification modules 30 is used to identify the positions where each the plurality of electrical stimulation modules 10 is located. Specifically, each the plurality of channel identification modules 30 is disposed around the peripheral of the plurality of channels 302 of the head cap 3. When each the plurality of electrical stimulation modules 10 is disposed in each the plurality of channels 302 of the head cap 3, each the plurality of channel identification modules 30 disposed around the peripheral of each the plurality of channels 302 is be electrically coupled or is to be electrically disconnected to each the plurality of electrical stimulation modules 10. When the connection between each the plurality of electrical stimulation modules 10 and each the plurality of channel identification modules 30 is in conduction circuit status, that is, each the plurality of electrical stimulation module 10 is electrically coupled to each the plurality of channel identification modules 30, and each the plurality of channel identification modules 30 will transmit a signal of conduction circuit status to the controlling module 20, so that the controlling module 20 will perform the procedure of adjusting and controlling the current intensity according to the amount of the changes in cerebral cortical blood flow detected by the optical probe 110. Then, the controlling module 20 provides the current with the current intensity to the electrode 100 to perform the stimulating process.

For example, when the channel identification module 30 is a jumper, some of the plurality of electrical stimulation modules 10 disposed in some of the plurality of channels 302, so that the jumper is electrically connected with some of the plurality of electrical stimulation modules 10 to form a circuit conduction status, the channel identification module 30 is provided for transmitting a signal corresponding to the circuit conduction status to the controlling module 20, and the controlling module 20 is provided for determining the desired sites of some of the plurality of electrical stimulation modules 10 where is corresponding to one of the plurality of brain areas of the human being according to the signal corresponding to the circuit conduction status.

In another embodiment, the short circuit status between each the plurality of electrical stimulation modules 10 and each the plurality of channel identification modules 30 means that when each the plurality of electrical stimulation modules 10 is disposed in each the plurality of channels 302, each the plurality of channel identification modules 30 is electrically disconnected with each other, so that the plurality of channel identification modules 30 will transmit a signal corresponding to the shot circuit states between each the plurality of electrical stimulation modules 10 and each the plurality of channel identification modules 30 to the controlling module 20, and then the controlling module 20 will not perform the regulating procedure of current intensity, and the electrical stimulation procedure is not to be performed by the electrical stimulation module 10.

In alternative embodiment, if the connecting status between each the plurality of electrical stimulation modules 10 and each the plurality of channel identification modules 30 is short circuit status, which means that when each the plurality of electrical stimulation modules 10 is disposed in each the plurality of channels 302, then each of the plurality of channel identification modules 30 is electrically disconnected with each other, so that the plurality of channel identification modules 30 will also transmit a signal corresponding to the short circuit status to the controlling module 20, and the controlling module 20 will perform the adjusting and controlling procedure of current intensity according to the amount of the changes in cerebral cortical blood flow detected by the optical probe 110. Then, the controlling module 20 provides the current with the suitable current intensity to the electrode 100, so as to the electrode 100 can perform the stimulating process. It is should be illustrated that the function and structure of electrical stimulation module 10 will be described in detail in subsequent description.

For example, the channel identification module 30 can be a photo sensor, some of the plurality of electrical stimulation modules 10 disposed in some of the plurality of channels 302, so that the photo sensor is disconnected with some of the plurality of electrical stimulation modules 10 to form the short circuit status, and the channel identification module 30 is provided for transmitting a signal corresponding to the short circuit status to the controlling module 20, and the controlling module 20 is provided for determining the desired sites of some of the plurality of electrical stimulation modules 10 where is corresponding to one of the plurality of brain areas of the human being according to the signal corresponding to the short circuit status.

The transcranial electrical stimulation system 1 also includes the power supply modules 40. The power supply module 40 is used to provide the power energy for the operation of transcranial electrical stimulation system 1. In another embodiment, the power supply modules 40 can provide the current with suitable current intensity to the electrode 100 controlled by the controlling module 20 to perform the stimulating process. Similarly, the detail operation of the transcranial electrical stimulation system 1 will be described below.

In another preferred embodiment, the transcranial electrical stimulation system 1 can be electrically coupled to the external controlling device 2 such as computer or mobile device. According to above discussions, when the optical probe 110 detected the amount of the changes in cerebral cortical blood flow of the brain area of the human being, the signal with the amount of the changes in cerebral cortical blood flow of the brain area of the human being can transmit to the external controlling device 2. The external controlling device 2 will regulate the current intensity emitted by the electrical stimulation module 10 which is to be performed with stimulating procedure based on the signal with the amount of the changes in cerebral cortical blood flow, and the external controlling device 2 gives the instruction to the controlling module 20 to provide the different current intensity corresponding to the signal with the amount of the changes in cerebral cortical blood flow to the electrode 100, so that the electrode 100 can perform the stimulation procedure. In the embodiment of the present invention, the current amount and the current intensity in the electrical stimulation module 10 for electrical stimulation is regulated by the controlling module 20 of the transcranial electrical stimulation system 1. In another embodiment, the amount of current and the current intensity in the electrical stimulation module 10 or electrical stimulation is regulated by the external controlling device 2.

In addition, the external controlling device 2 can also regulate the electrical stimulation module 10 to emit different current amount and different current intensities at the same time. In another embodiment, the external controlling device 2 can regulate the electrical stimulation module 10 to emit a constant current amount and a constant current intensity at the same time.

Figure 3:
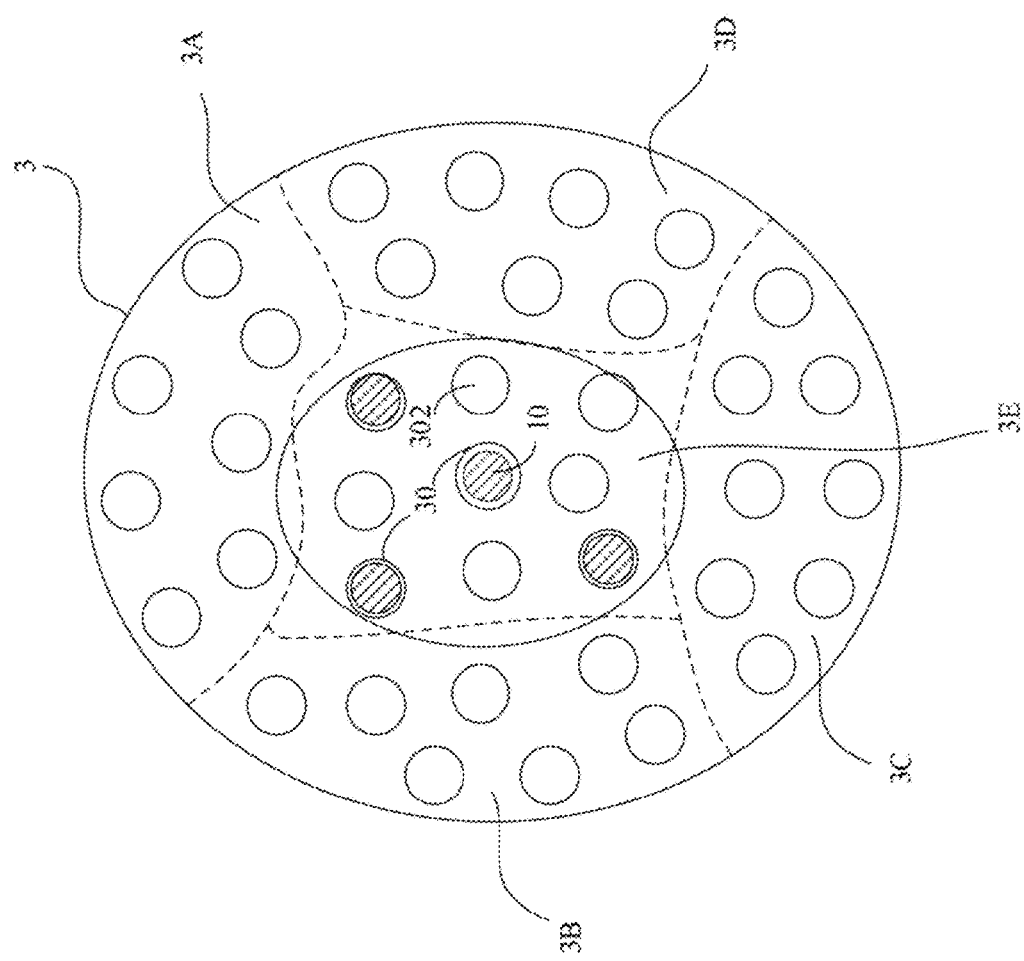
FIG. 3 is a schematic view of showing the head cap includes a plurality of brain regions corresponding to the brain area of the human being in accordance with the present invention disclosed herein.

Please also refer to FIG. 2 and FIG. 3. FIG. 2 shows the head cap with the plurality of electrical stimulation modules electrically coupled to the external controlling device, and FIG. 3 shows the head cap that includes a plurality of brain regions corresponding to the brain area of the human being, in which the plurality of brain regions is the area enclosed by the dotted line in FIG. 2. In FIG. 2, the head cap 3 includes a plurality of channels 302 therein. As discussed as abovementioned, each the plurality of channel identification modules 30 is disposed around each the plurality of channels 302, and the function of the plurality of channel identification modules 30 can identify the specific brain area where the plurality of electrical stimulation modules 10 is located. As shown in FIG. 3, the design of the plurality of channels 302 of the head cap 3 is corresponding to the brain area of the human being. Therefore, in this embodiment, the head cap 3 is divided at least five brain regions 3A-3E. Each brain regions 3A-3E of the head cap 3 is corresponding to the brain area of the human being, and each brain regions include a plurality of channels 302 therein. In one embodiment, when plurality of electrical stimulation modules 10 is disposed in one of five brain regions 3E of the head cap 3, the plurality of channel identification modules 30 around the plurality of channels 302 in the brain region 3E of the head cap 3 will identify where the plurality of electrical stimulation modules 10 is located, and the plurality of channel identification modules 30 will transmit a signal with the plurality of electrical stimulation modules 10 where is located to the controlling module 20 (as shown in FIG. 1), then the controlling module 20 can determine where the plurality of electrical stimulation modules 10 is located, for example, the plurality of electrical stimulation modules 10 is disposed in the plurality of channels 302 in the brain regions 3E of the head cap 3. Next, the controlling module 20 can regulate the current intensity emitted by the electrical stimulation module 10 in the brain regions 3E of the head cap 3 to perform the stimulation process.

In another embodiment, when the plurality of electrical stimulation modules 10 is disposed in the plurality of channels 302 in one of five brain regions, for example, brain region 3E, the plurality of channel identification modules 30 around the plurality of channels 302 will identify where the plurality of electrical stimulation modules 10 is located, and the plurality of channel identification modules 30 will transmit a signal with the plurality of electrical stimulation modules 10 where is located through the controlling module 20 (as shown in FIG. 1) to the external controlling device 2, then the external controlling device 2 can determine where the plurality of electrical stimulation modules 10 is located. For example, the plurality of electrical stimulation modules 10 is disposed in the plurality of channels 302 in the brain regions 3E. Next, the external controlling device 2 can regulate the current with suitable current intensity, and the signal corresponding to this current with suitable current intensities is transmitted to the controlling module 20, and the controlling module 20 will regulate the plurality of electrical stimulation modules 10 in the brain region 3E to emit the current with suitable current intensities corresponding to the signal to perform the stimulation process.

Figure 4:
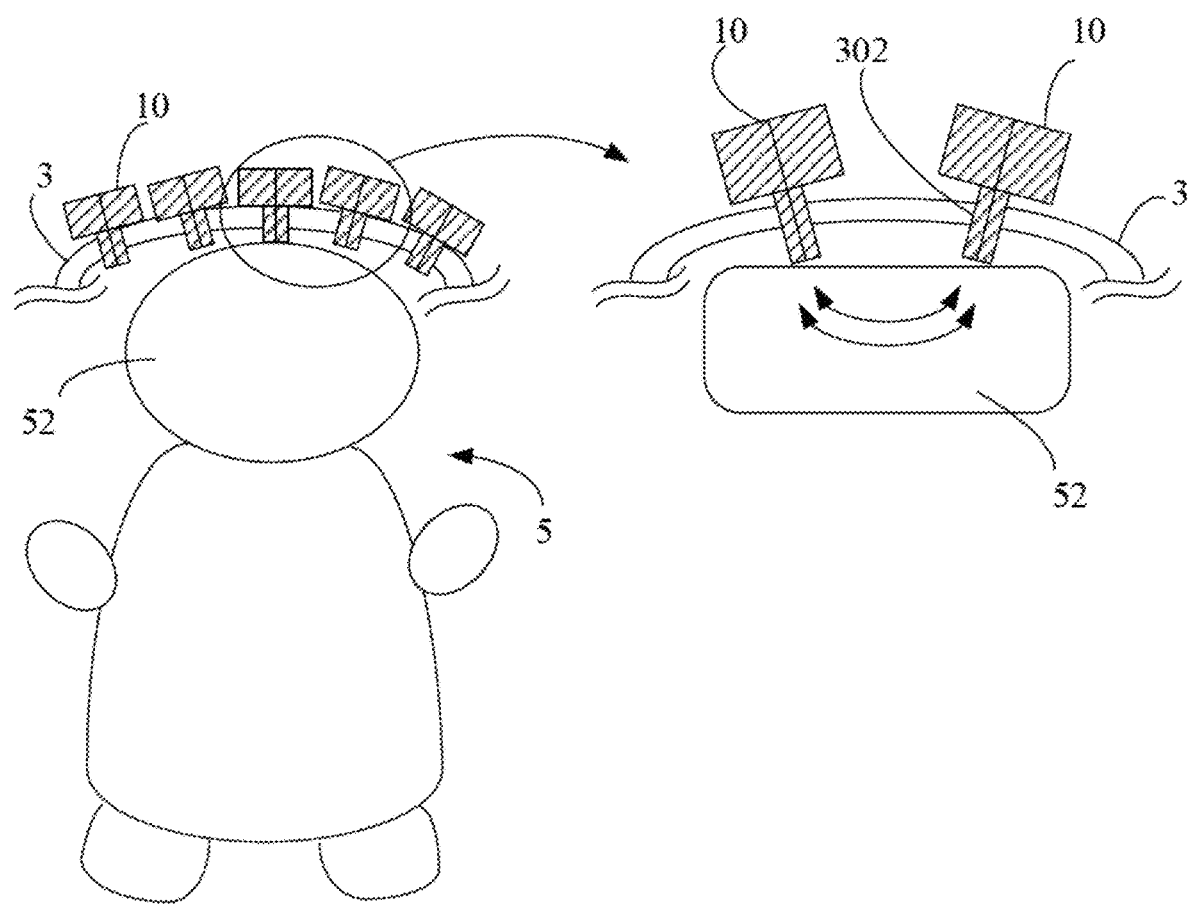
FIG. 4 is a cross-sectional view of showing the electrical stimulation module disposed in the channel of the head cap in accordance with the present invention disclosed herein.

Please also refer to FIG. 4. FIG. 4 shows that the user wears the transcranial electrical stimulation system on the head. In FIG. 4, user (human being) 5 wears the head cap 3 includes a plurality of electrical stimulation modules 10 therein on their head 52, in which the contact end of the plurality of electrical stimulation modules 10 is to be contacted the brain (head) of the human being 5. The electrical stimulation modules 10 are disposed in the channels 302 within the head cap 3 and the electrode 100 and the optical probe 110 are contacted to the brain area of the human being 5. In one embodiment, as shown in FIG. 5A, each electrical stimulation module 10a is hybrid optrode, which coaxially designed by electrode 100 and the optical probe 110, in which the electrode 100 is arranged around the optical probe 110.

Figure 5A:
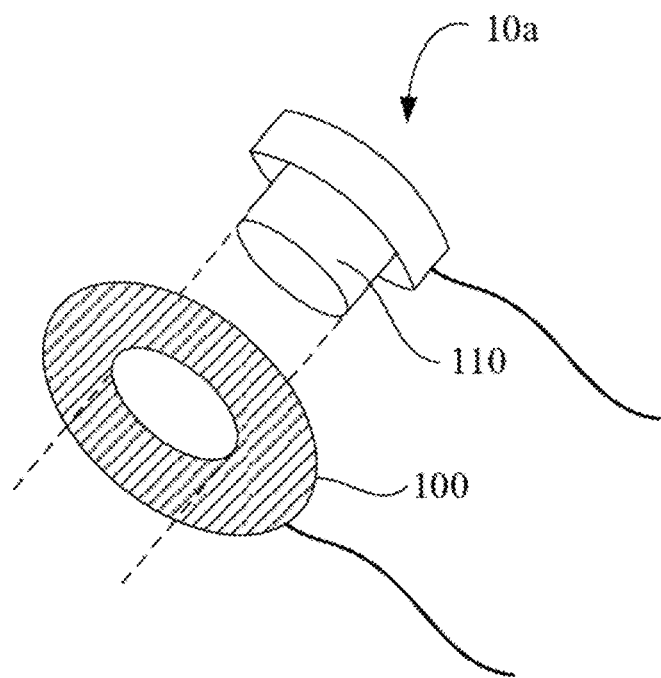
FIG. 5A is a schematic view of showing the electrode and the optical probe in the electrical stimulation module are coaxially designed in accordance with the present invention disclosed herein.
Figure 5B:
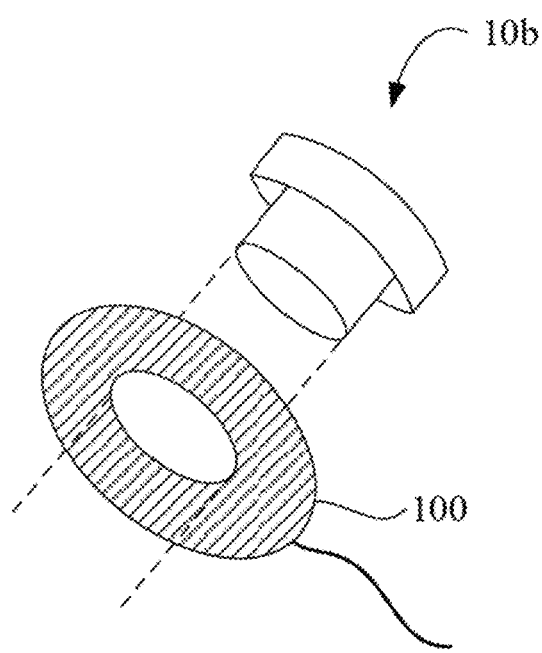
FIG. 5B is a schematic view of showing the electrode disposed in the electrical stimulation module in accordance with the present invention disclosed herein.
Figure 5C:
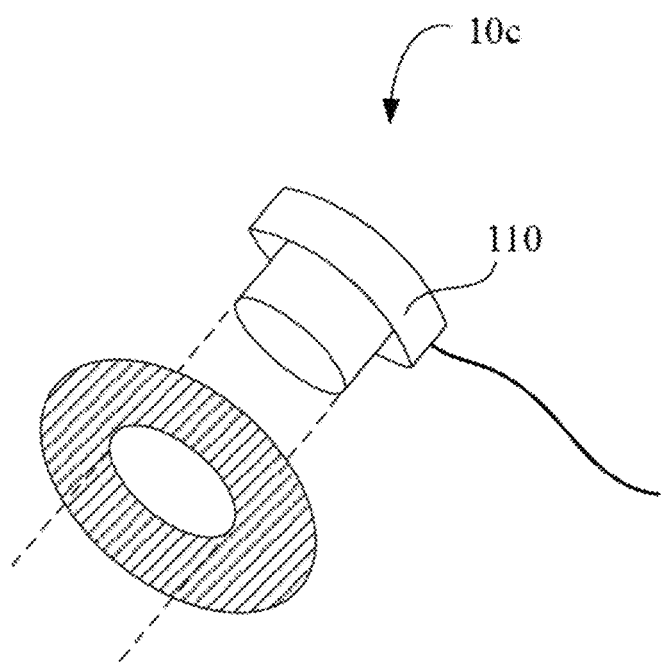
FIG. 5C is a schematic view of showing the optical probe disposed in the electrical stimulation module in accordance with the present invention disclosed herein.

In another embodiment, as shown in FIG. 5B and FIG. 5C, the arrangement of electrode 100 and the optical probe 110 is separated in different electrical stimulation modules 10b, 10c respectively, that is, at least one of the plurality of electrical stimulation modules 10b includes the electrode 100 (as shown in FIG. 5B), and another one of the plurality of electrical stimulation modules 10c includes the optical probe 110 (as shown in FIG. 5C), therefore, the cranial electrical stimulation and near infrared spectroscopy process can be operated between the electrode 100 and the optical probe 110 (as the arrow in FIG. 4). In this preferred embodiment, the electrical stimulation module 10b and 10c are used together, and the polarity of electrode 100 can be the positive or the negative.

Figure 6:
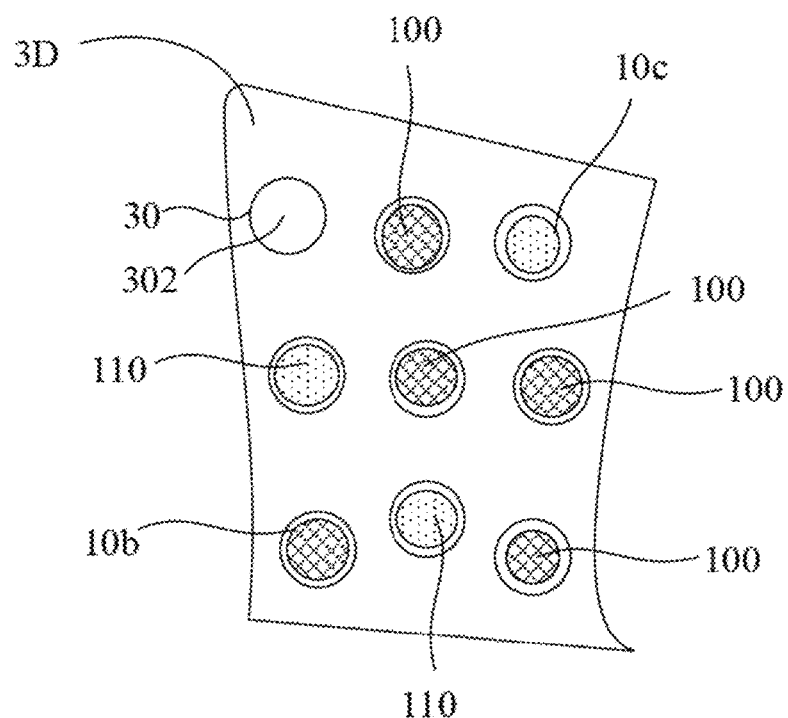
FIG. 6 is a schematic view of showing the electrical stimulation module disposed in the channel in a specific brain region of the head cap, and the optical probe and the electrode are separately arranged in different electrical stimulation module in accordance with the present invention disclosed herein.

As shown in FIG. 6, and with the description of FIG. 3 and FIG. 5A-FIG. 5C together. In FIG. 6, the arrangement of the electrode 100 and the optical probe 100 are separated in different electrical stimulation modules 10b, 10c, as shown in FIG. 5B and FIG. 5C. As shown in FIG. 6, in brain region 3D, the electrical stimulation module 10b with the electrode 100 therein and the electrical stimulation module 10c with the optical probe 110 disposed in different channel 302. In this embodiment, the polarity of the electrode 100 can be set as one positive electrode corresponds to one negative electrode, one positive electrode corresponds to multiple negative electrodes, one negative electrode corresponds to multiple positive electrodes, or multiple positive electrodes corresponds to multiple negative electrodes which can be set according to the needs of use. The polarity of the electrode 100 is adjusted by the external controlling device (not shown) or the controlling module (not shown). In FIG. 6, there are three electrical stimulation modules 10c with optical probe 110 disposed in the channels 302 of brain region 3D, optical probes 110 can detect the changes in cerebral cortical blood flow of the human being in the brain region 3D, and then the optical probes 110 will transmit the signal with the changes in cerebral cortical blood flow of the human being in the brain region 3D to the controlling module 20. The controlling module 20 will regulate the current intensity of the electrical stimulation module 10 corresponding the signal with the changes in cerebral cortical blood flow of the human being. In the present invention, according to Kirchhoff s current law, the total current intensity of the positive electrodes in some of electrical stimulation modules 10 should be equal to that of the negative electrodes in other electrical stimulation modules 10. Accordingly, the current will pass through electrodes 100 to stimulate the brain region 3D of the human being.

Figure 7:
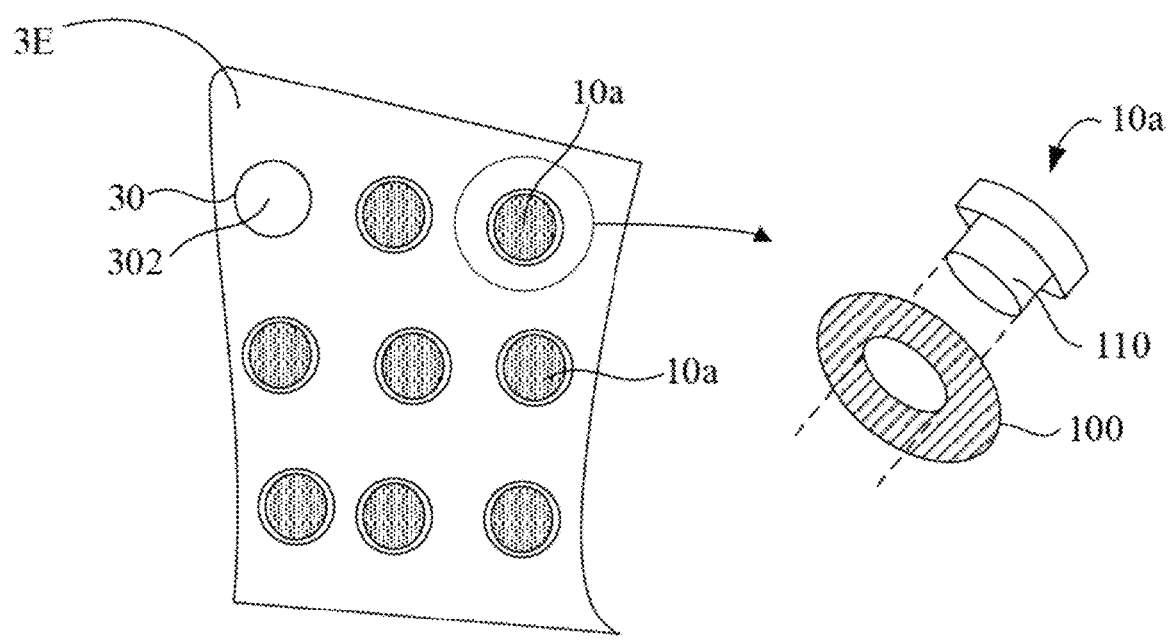
FIG. 7 is a schematic view of showing the electrical stimulation module disposed in the channel in a specific brain region of the head cap, and the optical probe and the electrode of the electrical stimulation module are coaxially designed in accordance with the present invention disclosed herein.

Please also refer to FIG. 7, and with the description of FIG. 3 and FIG. 5A together. FIG. 7 shows electrical stimulation module disposed in the channel in a specific brain region of the head cap, and the optical probe and the electrode of the electrical stimulation module are coaxially designed. The different between FIG. 7 and FIG. 6 is that the electrical stimulation module 10a is hybrid optrode, which the electrodes 100 and the optical probe 110 are coaxially designed also as shown as FIG. 5A. Therefore, the electrical stimulation module 10a can emit the current through the electrode 100 to perform the electrical stimulation procedure, and synchronously through the optical probe 110 to detect the changes in cerebral cortical blood flow in the brain region 3E of the human being. Furthermore, the polarity of electrode 100 of the electrical stimulation module 10a can be set as the positive or negative; similarly, the polarity of the electrode 100 can be set as one positive electrode corresponds to one negative electrode, one positive electrode corresponds to multiple negative electrodes, one negative electrode corresponds to multiple positive electrodes, or multiple positive electrodes corresponds to multiple negative electrodes which can be set according to the needs of use, and the polarity of the electrode 100 is adjusted by the external controlling device (not shown) or the controlling module (not shown).

For example, user can set the polarity of some of the electrode 100 of the plurality of electrical stimulation modules 10a as positive, others are negative. When the electrodes 100 of these electrical stimulation modules 10a perform the electrical stimulation procedure, the optical probe 110 in these electrical stimulation modules 10a synchronously detect the changes in cerebral cortical blood flow in the brain region 3E. The controlling module (not shown) is able to regulate current intensity of module 10 by the cerebral hemodynamic signal which is acquired by optical probe 110 of each electrical stimulation module 10a in the brain region 3E. According to Kirchhoff s current law, the total current intensity of the polarity of electrodes 100 in some of electrical stimulation modules 10 are positive that should be equal to that of the polarity of electrodes 100 are negative in other electrical stimulation modules 10. Accordingly, the current will passed through electrodes 100 to stimulate the brain region 3E of the human being.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A head cap with channel identification, comprising:
   a head cap, the head cap includes a plurality of channels and the head cap includes a plurality of brain regions corresponding to a brain of a human being;
   a plurality of channel identification modules, each the plurality of channel identification modules disposed around the peripheral of each the plurality of channels;
   a controlling module, the controlling module is connected with the plurality of channel identification modules; and
   a plurality of electrical stimulation modules, each the plurality of electrical stimulation modules disposed in the plurality of channels of the head cap,
   wherein when each the plurality of electrical stimulation modules disposed in each the plurality of channels and when the channel identification module is a photo sensor, some of the plurality of photo sensors and the some of the plurality of electrical stimulation modules are disconnected to form the short circuit status, the some of the plurality of photo sensors is provided for transmitting a signal corresponding to the short circuit status to the controlling module, and the controlling module is provided for determining the desired sites of some of the plurality of electrical stimulation modules disposed around the peripheral of each the plurality of channels of the head cap where is corresponding to one of the plurality of brain regions of the human being according to the signal corresponding to the short circuit status.

2. The head cap with channel identification according to claim 1, wherein the channel identification module is a jumper, some of the plurality of electrical stimulation modules disposed in some of the plurality of channels, so that some of the plurality of jumpers are electrically connected with some of the plurality of electrical stimulation modules to form a circuit conduction status, the channel identification module is provided for transmitting a signal corresponding to the circuit conduction status to the controlling module, and the controlling module is provided for determining the desired sites of some of the plurality of electrical stimulation modules where is corresponding to one of the plurality of brain regions of the human being according to the signal corresponding to the circuit conduction status.

3. The head cap with channel identification according to claim 1, further comprising a power supply module, and the power supply module is connected with the controlling module, and the power supply module is provided for providing the energy for an operation of the plurality of electrical stimulation modules and an operation of the controlling module.

4. The head cap with channel identification according to claim 1, further comprising an external controlling device, and the external controlling device is provided for regulating the current and the current intensity emitted by the electrical stimulation module.

5. The head cap with channel identification according to claim 4, wherein the external controlling device is further provided for regulating the different current amount and different current intensities emitted by each the plurality of electrical stimulation modules at the same time.

6. The head cap with channel identification according to claim 4, wherein the external controlling device can provide a constant current amount and a constant current intensity to the controlling module at the same time.

7. The head cap with channel identification according to claim 1, wherein the controlling module is provided for regulating the current and the current intensity emitted by the electrical stimulation module.

8. The head cap with channel identification according to claim 1, wherein the controlling module is further provided for regulating the different current amount and different current intensities emitted by each the plurality of electrical stimulation modules at the same time.

9. The head cap with channel identification according to claim 1, wherein the controlling module is further provided for regulating a constant current amount and a constant current intensity to the controlling module at the same time.

* * * * *